(12) United States Patent
Karstens

(10) Patent No.: US 8,883,469 B2
(45) Date of Patent: Nov. 11, 2014

(54) METHOD FOR PRODUCING ETHANOL BY FERMENTATION FROM LIGNOCELLULOSIC BIOMASS

(75) Inventor: Ties Karstens, Bötzingen (DE)

(73) Assignee: Zylum Beteiligungsgesellschaft mbH & Co., Patente II KG, Schönefeld/Waltersdorf (DE)

( * ) Notice: Subject to any disclaimer, the term of this patent is extended or adjusted under 35 U.S.C. 154(b) by 251 days.

(21) Appl. No.: 12/922,186

(22) PCT Filed: Feb. 10, 2009

(86) PCT No.: PCT/EP2009/000920
§ 371 (c)(1),
(2), (4) Date: Dec. 10, 2010

(87) PCT Pub. No.: WO2009/112134
PCT Pub. Date: Sep. 17, 2009

(65) Prior Publication Data
US 2011/0111474 A1    May 12, 2011

(30) Foreign Application Priority Data

Mar. 12, 2008    (DE) .......................... 10 2008 013 845

(51) Int. Cl.
*C12P 7/10* (2006.01)
*D21C 3/20* (2006.01)

(52) U.S. Cl.
CPC .. *C12P 7/10* (2013.01); *Y02E 50/16* (2013.01); *D21C 3/20* (2013.01)
USPC ......................................... 435/165; 435/161

(58) Field of Classification Search
USPC ................................................. 435/161, 165
See application file for complete search history.

(56) References Cited

U.S. PATENT DOCUMENTS

| | | | | |
|---|---|---|---|---|
| 4,091,749 | A  * | 5/1978 | Procter et al. | 162/25 |
| 5,473,061 | A  * | 12/1995 | Bredereck et al. | 536/59 |
| 8,211,189 | B2 * | 7/2012 | Guay et al. | 44/307 |
| 2004/0060673 | A1* | 4/2004 | Phillips et al. | 162/22 |
| 2008/0008783 | A1* | 1/2008 | Dale | 426/69 |
| 2008/0299628 | A1* | 12/2008 | Hallberg et al. | 435/139 |
| 2010/0081798 | A1* | 4/2010 | Balensiefer et al. | 530/500 |

FOREIGN PATENT DOCUMENTS

| | | |
|---|---|---|
| FR | 2 518 573 | 6/1983 |
| WO | WO 00/61858 | 10/2000 |
| WO | WO 02/29155 | 4/2002 |

OTHER PUBLICATIONS

Shah et al.; "Effect of Pretreatment on Simultaneous Saccarification and Fermentation of Hardwood into Acetone/Butanol," Applied Biochemistry and Biotechnology; vol. 28/29, 1991, pp. 99-109.*
Shah et al.; "Effect of Pretreatment on Simultaneous Saccharification and Fermentation of Hardwood into Acetone/Butanol", Applied Biochemistry and Biotechnology; vol. 28/29, 1991, pp. 99-109; XP008114715.

* cited by examiner

*Primary Examiner* — Jon P Weber
*Assistant Examiner* — Kara Johnson
(74) *Attorney, Agent, or Firm* — Fay Sharpe LLP

(57) ABSTRACT

The description relates to a method of producing bioethanol by separating lignin from a crushed lignocellulose biomass and obtaining cellulose and, if required, hemicellulose and additionally processing the cellulose or the mixture of cellulose and hemicellulose to form sugars and subsequently form bioethanol. The method is characterized in that crushed lignocelluloses biomass is treated with an alkanolamine for extracting the lignin therein, the lignin solution is separated, the residue containing cellulose/hemicellulose is converted to sugars without drying, and the sugars are fermented to obtain bioethanol. The raw cellulose (cellulose/hemicellulose), owing to its high reactivity, can easily be converted into sugar, which can be fermented to form bioethanol.

19 Claims, No Drawings

METHOD FOR PRODUCING ETHANOL BY FERMENTATION FROM LIGNOCELLULOSIC BIOMASS

The invention relates to a method of producing bioethanol by separating lignin from a crushed lignocelluloses biomass and obtaining cellulose and, if required, hemicelluloses and further processing of the cellulose or mixture of cellulose and hemicellulose to obtain sugars and subsequently obtain bioethanol.

Lignocellulose biomass, a source of fermentable sugar, has not hitherto been used on an industrial scale. In contrast however to starch-containing raw materials such as cereals (maize, wheat, etc), enzymatic decomposition of the polysaccharides in the hemicellulose biomass to sugar is difficult. The resistance of the lignocellulose biomass to enzymatic hydrolysis occurs particularly at the crystalline phase of the cellulose, at the accessible surface, at the lignin coating and finally at the hemicelluloses screening the cellulose.

Pretreatment of the biomass is necessary in order to improve access to the cellulose for enzymes for converting carbohydrates into sugar. The pretreatment of the lignocellulose biomass is therefore the key to improving the efficiency and reducing the cost of cellulose bioethanol. To obtain effective pretreatment, it is important to not crush the biomass excessively by mechanical means, to preserve the pentose fraction as far as possible, and to restrict the formation of by-products which reduce the efficiency of the enzymes. In addition, the energy consumption and cost of pretreatment should be kept at a minimum. Finally, it is desirable to obtain the lignin and sell it as a by-product.

These important aspects of industrial use of lignocellulose biomass for producing ethanol are summarised in "Features of promising technologies for pretreatment of lignocelluloses biomass" by Nathan Mossier et al, Bioresource Technology 96 (2005) 673-686. D. Fengel and G. Wegener come to similar conclusions in their monograph "Wood, Chemistry, Ultrastructure, Reactions", De Gruyter, Berlin, N.Y. 1989. There are two main obstacles to hydrolysis of cellulose to glucose. The main obstacle occurs at the lignin, which can reduce the enzymatic action on the cellulose to a minimum. In addition the cellulose itself, owing to its crystallinity in the naked cell wall, offers strong resistance to chemical or enzymatic attack.

The known methods in the prior art each have specific disadvantages.

In the steam explosion method, the hemicelluloses are substantially hydrolysed by steam at high temperature, thus improving the accessibility to enzymes, but the enzymes are inhibited by the acids involved. In treatment with hot water under pressure at temperatures above 200° C., a large part of the biomass is soluble. However, the hemicelluloses decomposed to form sugars go on to form aldehydes such as furfurals, which are strong enzyme inhibitors.

Treatment with dilute acid has some serious disadvantages. Owing to the risk of corrosion, the reactors have to be made of very expensive materials. The acid needs to be neutralised with lime before the sugar is fermented. The resulting formation of gypsum has a negative effect on solubility. The liquid components have to be purified via ion exchangers before enzymatic hydrolysis. The output is also reduced by formation of decomposition products and enzyme inhibitors. Other disadvantages are presented by the removal of gypsum, the long duration of enzyme treatment, and by the very energy-intensive grinding of the biomass.

Pretreatment with ammonia admittedly results in a high degree of delignification, so that the use of enzymes can be reduced. The crystalline character of the cellulose is also altered (the lattice changes from cellulose I to cellulose II), which slightly increases the accessibility. The disadvantage, however, is the high cost of ammonia recovery.

The prior art also contains the following information:

One disadvantage of industrially used cellulose processes is undoubtedly the loss of reactivity as a result of drying. On the other hand "never-dried pulp" (cellulose dried until the moisture content after digestion and bleaching is not below 30%) is highly reactive. The fibre formed after digestion is therefore much more suited for chemical further processing.

In steam explosion processes in the prior art, pressures above 20 bar are commonplace in order to exceed the softening temperatures of lignin and polyoses. The high steam temperatures (over 200° C.) resulting from these high pressures, however, result in severe breakdown of the cellulose chains and also lead to condensation of the lignin, which becomes more difficult to extract. Penetration of steam into crystalline regions of the lignocellulose structure is unlikely, and consequently modifications cannot be made in this respect. The prior art of steam explosion is described in a number of patents, relating mainly to the technical design and the basic features of the process. Most studies have been made by using wood as the raw material. In most cases the main stress is on optimising the severity factor (the integral of the product of the steam temperature and the duration of action).

The disadvantage of using steam is that additives cannot be added to the steam without great technical expense, if at all. Instead, the biomass must be brought into contact with the reactants before the steam explosion, which is usually accompanied by poor distribution or higher proportioning. Similar remarks apply to the steam refining process (steam digestion processes followed by mechanical unravelling), which use less high-pressure steam (10-15 bar) and mechanical devices for unravelling. The only fully continuous cellulose digestion process used on an industrial scale is the steam explosion of wood chips or other biomasses, using the Stake System II of Messrs StakeTech Stake Technology.

In connection with pulping (digestion of cellulose) there are two different uses of ammonia in the prior art: defibration of lignocellulose materials by using ammonia for plasticising at high temperature by explosive expansion (J. J. Connor Tappi 55(3), (1972) 353-358) and plastification of wood chips in an Asplund refiner under pressure using ammonia. Unravelling of wood required much less energy (R. C. Peterson and R. W. Strauss, J Polymer Sci. C36 (1971) 241.250). In both cases, lignin could not be removed to a significant extent.

The use of alkanolamines for removing lignin from lignocelluloses was first described by Elton Fisher and R. S. Bower (J. Am. Chem. Soc. 63 (1941) 1881-1883). Monoethanolamine was used in the seventies as an additive to caustic soda for digestion of wood (catchwords: alkaline pulping in aqueous alcohols and amines, acceleration of soda delignification, sulphur-free delignification). The aim was reduction or replacement of sulphur-containing chemicals.

One problem was to process the digestion chemicals caustic soda and ethanolamine and separate the lignin. Lignin is usually obtained from caustic soda by precipitation with addition of acid. Production of lignin in this way from the solution of caustic soda and alkanolamine has certainly not facilitated the processing and recovery of the digesting chemicals. Conventional combustion of the lignin in the NaOH after concentration, the first step of NaOH recovery, also results in loss of alkanolamine, which is very expensive.

The aim of the invention therefore is to provide a method of fractionating lignocellulose-containing biomass wherein the said disadvantages of the prior art are largely eliminated. The components lignin on the one hand and hemicellulose/cellulose on the other hand need to be separated from one another in a form substantially free from impurities in order to obtain these raw materials for further processing. The need is for a sulphur-free and chlorine-free wood digestion process which also works without caustic soda and thus without expensive reclaiming and purification of exhaust air and outgoing water. More particularly the production of chemical cellulose needs to be carried out in time, chemical and energy-saving manner in a small decentral unit. The resulting cellulose/hemicellulose is first converted to sugar and then to bioethanol. The end result therefore is a particularly advantageous method of producing bioethanol by modified prior art in order to obtain reactive cellulose and hemicellulose from lignocellulose biomass.

To this end the invention provides a method of producing bioethanol by separating lignin from a crushed lignocelluloses biomass and obtaining cellulose and, if required, hemicellulose and further processing of the cellulose or mixture of cellulose and hemicellulose to obtain sugars and subsequently obtain bioethanol, characterised in that crushed lignocellulose biomass is treated with an alkanolamine for extracting the lignin therein, the lignin solution is separated, the cellulose/hemicellulose-containing residue is converted to sugar without drying, and the sugar is fermented to obtain bioethanol.

Advantageous other features of the method are disclosed in the accompanying claims 2 to 16.

The method according to the invention enables lignocelluloses to be digested and decomposed into their components, after which the residue is extracted with alkanolamine in order to obtain raw cellulose (cellulose/hemicellulose).

Any kind of lignocellulose can be used for the teaching according to the invention, i.e. fractionation into the main constituents (cellulose, polyoses and lignin). The lignocellulose-containing biomass can be any of a wide variety of plant growth materials such as wood, oat husks, maize or corn stalks, bagasse, or any kind of straw, e.g. wheat, rice, oat or rye or maize straw. Fibrous raw materials such as annual plants can be chopped into suitable fibres.

The next step is optional treatment with ammonia. This can be performed at any suitable place after the said washing step, using aqueous ammonia solution, ammonia gas or liquid ammonia. Preferably the proportion by weight of liquid ammonia to the treated substance (relative to dry substance) is adjusted to about 0.1:1 to 4:1.

The alkanolamine may in particular be any which are not substituted with alkyl groups on the nitrogen. This eliminates e.g. N-methyl monoethanolamine and N,N-dimethyl monoethanolamine, since these have no effect on extraction of lignin from wood.

The extraction agent is preferably monoethanolamine, which can be used in preheated form, especially at least at about 80° C. It has been found that the extraction effect of not pretreated lignocellulose biomass increases appreciably after pretreatment with ammonia. Under similar extraction conditions, the lignin content of the extract from biomass treated with ammonia is about 60% higher than in untreated biomass.

Extraction according to the invention occurs preferably under pressure, e.g. in a suitable autoclave or a continuous extractor. Equally good results can be obtained by extraction at atmospheric pressure, e.g. in the case of straw.

In batch operation, i.e. in an autoclave, the biomass and the water therein, washed free from hemicelluloses and optionally crushed and suitably pretreated with ammonia, is heated to a temperature of about 80° C. to 150° C., particularly 100° C. to 140° C., preferably for at least 10 minutes, particularly for at least half an hour. Solvents for the resulting lignin decomposition components can already be added.

Continuous extraction is preferable to batch operation. This can be performed by sending a flow of preheated extraction agent through the lignocellulose biomass poured into a pressure reactor, or by conveying the material for extraction, i.e. the lignocellulose biomass, in countercurrent with the extraction agent. Both methods have an advantage over the autoclave, i.e. stationary operation, in that side reactions are substantially eliminated by removing the decomposition products with the extraction agent. Without altering the extraction effect, operation can be at a lower temperature with a lower liquor ratio of extraction agent to lignocellulose biomass. The solubility of organisolv lignin in monoethanolamine is relatively high (250 g per liter).

In a preferred embodiment of the invention, extraction occurs in a number of stages, i.e. at least two successive extractions with alkanolamine. Preferably the same total quantity of alkanolamine is used as in single-stage extraction. Extraction in counter-current is advantageous here, since the shortest extraction times are obtained.

Monoethanolamine (hereinafter called MEA for short) extraction agent has various advantages. During digestion, MEA prevents lignin condensation and grafting on to cellulose, protects the cellulose from DP decomposition and improves delignification.

Extraction using alkanolamine can be performed at relatively low temperatures (about 100 to 120° C.) particularly in the case of ammonia pretreatment. In spite of the lower temperatures, low kappa numbers are then obtained, and side-reactions are greatly reduced.

After the extraction stage, the raw cellulose (cellulose/hemicellulose) is obtained. To this end the lignin extract (very dark brown or black) is separated from the raw cellulose fibres in suitable manner by the conventional methods of separating liquid from solids. If the residues of process-modified lignin in the raw cellulose need to be completely removed, they can be extracted by a suitable solvent by washing or contra-current washing. The solvent used is then separated by distillation from the lignin and from the extraction agent, and is thus recovered for further use.

The residue after distillation of the solvent can also be combined with the extract separated from the fibres. The water and the alkanolamine extracting agent can thus be separated by distillation, preferably vacuum distillation. Other separation processes are suitable here, optionally for concentrating the lignin extract—down to the dry substance in the extreme case. The lignin can also be separated by adding a non-solvent to the solution of lignin in alkanolamine. The lignin is precipitated in the form of solid particles and can be separated from the alkanolamine extraction agent by a suitable solid/liquid separation process such as filtering, centrifuging, thin-film evaporation or membrane separation methods. The lignin can be separated e.g. by introducing $CO_2$ into the water or preferably with the washing water after extraction with alkanolamine of the dilute, optionally concentrated, lignin/alkanolamine extract. Most of the alkanolamine is recovered in pure form by concentration by thin-film evaporation or another suitable distillation method. The remaining alkanolamine is distilled after distilling off the water from the precipitated liquid and separating the lignin (likewise in vacuo). The lignin is thus precipitated by introduction of $CO_2$ and centrifuging. The addition compound formed with the $CO_2$, i.e. alkanolamine*$CO_2$, can be completely decomposed into alkanolamine and $CO_2$, either by heating or by spraying in steam. The residue consists of lignin of much lower molecular weight but chemically unchanged.

This can therefore be used as a chemical raw material, e.g. for production of thermosetting plastics or polyurethanes.

The raw cellulose has a kappa number of not more than about 20, preferably below about 10. This corresponds to a lignin content of <3 or <1.5 wt. % and is an advantageous first step in enzymatic saccharification of the raw cellulose.

An "inclined screw reactor" can be used in practice. An "inclined screw reactor" is preferably used e.g. for treatment with $NH_4OH$/alkanolamine, followed by said unravelling for thorough lignin extraction in counter-current. These two steps result initially in a low-lignin, high-water fraction which can be repeatedly used, thus concentrating the lignin, while the result in the second case is a high lignin, alkanolamine-rich fraction. The two fractions are combined in the ratio of approximately 2/1 water-rich/alkanolamine-rich, enabling the lignin to be precipitated by $CO_2$ at elevated temperature. Only a little water needs to be distilled off the alkanolamine-rich low-water fraction, in order to recover most of the alkanolamine, e.g. by thin-layer evaporation, and simultaneously increase the lignin concentration by more than 20%.

The invention has a number of advantages:

One advantage is that no sulphur-containing chemicals need to be used for digestion.

If the raw material is straw as already mentioned, there will be no need for conventional recovery or wet oxidation, which is multi-stage and expensive in the case of NaOH. Alkanolamine is recycled by simple vacuum distillation. The addition compound alkanolamine*$CO_2$ formed between alkanolamine and $CO_2$ can be completely decomposed into alkanolamine and $CO_2$ by spraying in steam. There is no need to recover sodium salts. Owing to the low water content of straw, alkanolamine can also be extracted without pressure, thus simplifying the apparatus.

The invention also permits extraction with an alkanolamine with much lower liquor ratios (about 3:1), particularly in continuous operation. This also advantageously affects the steam consumption during extraction and recovery (about 3:1 to 1:1) in contrast to conventional digestion processes.

Small decentralised units for producing raw cellulose can be operated under optimum economic conditions if the alkanolamine extraction agent needs to be recycled. The use of alkanolamine as an extraction agent is therefore advantageous in two respects. Recovery of these materials by distillation is not energy-consuming, owing to their natural heat of evaporation. Lignin can be separated without using acids, which also avoids complicated processes and spares the environment.

There is also no need for additives for preventing condensation of lignin, which saves costs. As there is no need for pretreatment with chemicals, as in exclusively steam explosion and steam refining processes, there is no need problem in distribution thereof.

After extraction with alkanolamine, raw cellulose has greater decrystallisation than in other processes. This is undoubtedly advantageous for further processing to bioethanol, since uniform accessibility for sugar-producing enzymes is ensured. Ammonia can be used in much smaller proportions than in exclusively ammonia explosion of biomass, which also advantageously affects the operating costs. Expensive recovery of liquid ammonia is unnecessary.

Since the time required for saccharification naturally decreases with the kappa numbers (the lignin content) after extraction, the method according to the invention provides good working conditions. As a result of the fully continuous operation, the specific investments are lower and the space-time yields are high. Simple commercially-available plant components can be used.

This ensures economic operation even in small plants. The alkanolamine recovery circuit can be closed, thus reducing the expense of concentration, water consumption and energy during distillation.

If alkanolamine extraction in the process according to the invention is multi-stage or continuous instead of single-stage, there will be advantages regarding efficiency and productivity of the process.

Continuous operation has other advantages: There is no need to displace one process liquid by another, as in conventional pulping technology in digesters. In digesters the exchange and washing processes are less effective and therefore relatively lengthy. In addition the separation effect during displacement results in practice in undesired mixing or uncertain transitions, thus increasing the expense of recovery. In a continuous process, the apparatus does not need to be designed for high pressures.

As already described, according to the invention a lignocellulose biomass is advantageously converted to cellulose/hemicellulose having particularly high reactivity. According to the invention this product is converted to sugars in professional manner, and the sugars are fermented to form bioethanol. This professional knowledge will now be set out:

Cellulose substances, i.e. cellulose/hemicellulose freed from lignin according to the invention, are broken down by cellulases. This term always relates to a mixture rather than to single enzymes. Cellulases are produced by microbes such as bacteria and fungi, e.g. *Trichoderma*. The main constituents of cellulases are β-1,4 gluconases, which bring about the primary hydrolytic cleavage of the β-1,4 glycoside bonds between the anhydroglucose units in the cellulose chain.

There are two kinds of hydrolytically active enzymes, i.e. 1) endo-enzymes (endo-β-1,4-gluconases) which split glycoside bonds at various places on the cellulose molecules in order to form oligomeric mixtures of chain fragments and 2) exo-enzymes (exo-β-1,4-gluconases), which split glycoside bonds in the cellulose molecules at places near the non-reducing chain ends, resulting in low-molecular fragments, mainly cellobiose or glucose. There are also oxidising enzyme systems, usually called gluco-oxidases. The part played by them in enzymatic breakdown is still under discussion. Further clarification of terms and a brief classification of the enzymes participating in enzymatic breakdown of cellulose are given by P. Finch and J. C. Roberts (1985) in "Enzymatic Degradation of Cellulose" in: Cellulose Chemistry and Its Application (Eds: T. P. Nevell and S. H. Zeronian), chapter 13, page 312) Ellis Horward Limited, Chichester.

Sugar, particularly hexose sugar, is usually fermented with the yeast *saccharomyces cerevisiae* whereas pentose sugar (xylose) is fermented with the *Fusarium* spec. fungus. In mixed cultures for hydrolysis and fermentation of xylose, two anaerobic thermophilic bacteria, i.e. *Clostridium thermocellum* and *Thermoanaerobacter ethanolicus*, are used in the presence of cellulose material. In industrial enzymatic hydrolysis the enzymes, e.g. *Z. Mobilis*, are produced in situ. Enzymatic hydrolysis and fermentation are preferably performed in one step, i.e. simultaneous saccharification and fermentation (SSF).

In all cases, effective pretreatment, such as pretreatment with MEA, is an important step with regard to the efficiency and duration of enzymatic hydrolysis.

When working on the invention, the inventors made various discoveries which facilitate understanding of the invention. The details are as follows:

Pretreatment with alkanolamine, particularly monoetherolamine (MEA) of ligno-cellulose biomass is free from many of the disadvantages of the prior art as described. Monoethanolamine can specifically break down and dissolve lignin. On the other hand it has a protective effect on polysaccharides, i.e. cellulose/hemicellulose, since unlike other alkalis (e.g. caustic soda) it does not break down the polysaccharide chains (peeling reaction). In addition to complete removal of lignin, MEA has a steeping effect on cellulose and hemicelluloses.

For example the degree of fibrillation and the size of crystallites are reduced, resulting in wider spaces and a higher proportion of accessible surface. This has been shown by measurements of the water and acetic acid retaining capacity. The proportion of amorphous structures is increased, as shown by X-ray diffraction.

The solvent retention capacity, a measure of the accessibility, is 108% for MEA and 51% for water. Amines, as known, can decrystallise cellulose substrates. Treatment with ethylamine increases the proportion of disordered (decrystallised) cellulose from 9% to 70%. An important factor as regards the decrystallising effect is the "pKa value" which measures the basicity, which in turn is important for breaking down the hydrogen bridge compounds. MEA, at concentrations of more than 50% in water, has a pH of 12.5. After pretreatment with MEA, the lignin dissolved in MEA can be almost quantitively removed by washing with hot water. There is no effect on the steeping of cellulose and hemicellulose by pretreatment with MEA. Steeping occurs within the fibrils, i.e. in the crystalline cellulose fibrils, and also between fibrils. Treatment of cellulose with liquid ammonia is an example of effective intracrystalline steeping. Ammonia penetrates into the crystalline regions, thus widening the spaces between the 101 planes of the crystal lattice.

The degree of accessibility can also be determined by iodine absorption through the samples, which have been variously treated. The size of the iodine molecules limits absorption thereof on the amorphous regions of the sample. The degree of iodine absorption is thus directly dependent on the proportion of amorphous regions. Untreated cellulose typically absorbs ≈50 mg iodine/g sample, corresponding to a proportion of about 15% in the amorphous phase (determined by X-ray diffraction measurements of the crystallinity of the same sample). Samples of biomass treated with gaseous ammonia, steeped in liquid ammonia or delignified with MEA have 125, 160 and 230 mg of iodine absorbed per g sample respectively. The accessibility to enzymes of the sample delignified with MEA is therefore about 4.6 times greater than in the case of untreated cellulose, i.e. the proportion of easily accessible amorphous regions is 15*4.6≈70%.

The water bridge bonding capacity of the species interacting with cellulose is of primary importance. Particularly high steeping can be obtained with liquids which are non-associated proton acceptors. The following are examples: ammonia (pKa=9.25), methylamine (pKa=10.69), ethylamine (pKa=10.81) and monoethanolamine (pKa=9.5). MEA thus has a pKa value near that of ammonia.

Solutions of ammonia in the ethernolamine can steep the cellulose and not only change the structure; the cellulose lattice expanded by ammonia can expand further. For example the water retention capacity (WRV) of cellulose in water containing 10% ammonia is not more than 50%. On the other hand, in 10% ammonia in MEA the WRV increases to 115%. This indicates that MEA assists the penetration of ammonia into the cellulose lattice and the cellulose lattice expanded by ammonia is expanded further. This suggests that small quantities of ammonia in MEA are advantageous. This applies not only to the increased accessibility to enzymes but also to the neutralising effect of ammonia on the acid groups (acetyl, uronic and formyl radicals) bonded in the lignocelluloses.

Treatment of lignocellulose biomass according to the invention therefore has numerous advantages. Separation of salts is avoided, since no acids are used. Enzyme inhibitors do not need to be removed by ion exchange before enzymatic hydrolysis. More than 95% of the lignin is removed from the biomass. This lignin is an organosolv lignin, similar to lignin obtainable by the Acell process, and can alternatively be used for generation of steam and subsequent generation of electricity. Owing to the tarry consistency of lignin freed from MEA by distillation, no expensive biomass boilers are needed for steam generation. Alternatively the lignin can be precipitated and sold e.g. for producing polymers, long-time fertilisers etc. The lignin can advantageously be precipitated by using the carbon dioxide produced in large quantities during fermentation of sugar to ethanol. The MEA pretreatment process thus meets a requirement, i.e. producing a higher-value by-product. The advantage of separation of lignin, compared with other processes, is that the enzyme reaction speed is higher by a factor of 3-5.

In addition, smaller apparatus can be used, owing to the separation of the lignin component of the biomass, which accounts for about 18-25% by weight. In addition, after the lignin and the monoethanolamine have been removed by washing, the solid content of the delignified fibres is about 40-45%, which also likewise enables the capacity of the enzyme reactor to be reduced. This has a very positive effect on the cost of producing bioethanol.

Finally, pretreatment with MEA according to the invention meets the requirement "low energy, high yield, no detox", which is a slogan in the industrial production of bioethanol from lignocellulose biomass.

The invention will now be illustrated in detail with reference to an example:

EXAMPLE 1

A biomass treated with ethanolamine and subsequently freed from lignin and ethanolamine with hot water was poured into a flask containing 50 ml citrate buffer (pH 4.5) so that the concentration was 2 wt. %. The flask was autoclaved at 120° C. 2 ml cellulase (3-4 IU/g of pretreated biomass) was added. Hydrolysis was effected at a constant temperature of 50° C. in a water bath, shaking the flask. The sugar was analysed by HPLC. After 36 hours the conversion rate to glucose and xylose reached a constant value. The yields of glucose and xylose were 90% and 85% respectively. The mixture was then subjected to conventional fermentation.

Fermentation was effected by using the bacterium *Z. mobilis* with addition of diamonium phosphate. This biocatalyst converts glucose and xylose into ethanol. The yield of ethanol was 90% from glucose and 85% from xylose.

The invention claimed is:
1. A method of producing bioethanol by separating lignin from a crushed lignocelluloses biomass and obtaining cellulose and further processing of the cellulose or mixture of cellulose and hemicellulose to obtain sugars and subsequently obtain bioethanol, characterised in that crushed lignocelluloses biomass is treated with an alkanolamine as a solvent for extracting the lignin therein for at least 10 minutes at a temperature of about 80° C. to 150° C., the extraction of lignin carried out in the absence of caustic soda;

the lignin solution is separated;
the residue containing cellulose/hemicellulose is converted to sugars without drying;
the sugars are fermented to obtain bioethanol; and wherein before the extraction of the lignin, the lignocellulose biomass is treated with ammonia gas or aqueous ammonia solution.

2. A method according to claim 1, characterised in that the lignocellulose biomass is in the form of straw, grass, bagasse, poplar and/or bamboo.

3. A method according to claim 1, characterised in that during extraction of the lignin an additional solvent for lignin is used.

4. A method according to claim 3, wherein the additional solvent is one which swells the cellulose and hemicellulose.

5. A method according to any of claim 1, characterised in that extraction is continued for at least half an hour at a temperature of about 100° C. to 140° C.

6. A method according to any of claim 1, characterised in that the alkanolamine is heated before extraction.

7. A method according to claim 6, wherein the alkanolamine is heated to a temperature of at least about 80° C.

8. A method according to claim 1, characterised in that the alkanolamine is monoethanolamine.

9. A method according to claim 1, characterised in that after extraction of the lignin, the lignin solution adhering to the residue is removed by an additional solvent.

10. A method according to claim 9, characterised in that the lignin solution adhering to the residue is removed by washing or washing in countercurrent with the additional solvent, after which the additional solvent is separated from lignin and the extraction agent alkanolamine by distillation and recovered.

11. A method according to claim 1, characterised in that the lignin solution adhering to the residue is removed by squeezing out or centrifuging.

12. A method according to claim 1, characterised in that the lignin dissolved in the alkanolamine is precipitated by adding a non-solvent and separated by solid/liquid separation processes.

13. A method according to claim 12, characterised in that the precipitated lignin is separated from alkanolamine by filtering or centrifuging.

14. A method according to claim 13, characterised in that the lignin dissolved in alkanolamine is separated in a thin-film evaporator or by a membrane process.

15. A method according to claim 1, characterised in that the residue containing a cellulose/hemicellulose is converted to sugar by treatment with a cellulase.

16. A method according to claim 1, characterised in that the sugar obtained from cellulose and hemicelluloses is fermented to form bioalcohol by adding and fermenting with yeast.

17. A method according to claim 1, wherein the ammonia gas or aqueous ammonia solution is ammonia gas.

18. A method according to claim 1, wherein the ammonia gas or aqueous ammonia solution is aqueous ammonia solution.

19. A method according to claim 1, wherein the lignocellulose biomass is in the form of straw.

* * * * *